(12) United States Patent
Watanabe

(10) Patent No.: US 7,990,587 B2
(45) Date of Patent: Aug. 2, 2011

(54) ELECTRONIC ENDOSCOPE HAVING AN APPARATUS FOR CONTROLLING A SHADING MEMBER

(75) Inventor: Yasuharu Watanabe, Tokyo (JP)

(73) Assignee: Hoya Corporation, Tokyo (JP)

( * ) Notice: Subject to any disclaimer, the term of this patent is extended or adjusted under 35 U.S.C. 154(b) by 1063 days.

(21) Appl. No.: 11/249,497

(22) Filed: Oct. 14, 2005

(65) Prior Publication Data

US 2006/0082845 A1    Apr. 20, 2006

(30) Foreign Application Priority Data

Oct. 15, 2004 (JP) ................ P2004-301443

(51) Int. Cl.
*H04N 1/46* (2006.01)
(52) U.S. Cl. ........... 358/509; 348/65; 348/45; 348/68; 348/69; 600/101; 600/164; 600/160; 600/248; 600/178; 600/179; 600/180; 600/181; 600/182; 385/117; 396/17; 359/385; 359/390; 359/230; 359/236
(58) Field of Classification Search .......... 358/509, 358/443, 296, 1.9; 348/45, 65, 68–69; 359/385, 359/390, 230, 236; 600/101, 164, 160, 248, 600/178–182; 385/117; 396/17
See application file for complete search history.

(56) References Cited

U.S. PATENT DOCUMENTS

| | | | | |
|---|---|---|---|---|
| 5,812,187 A | * | 9/1998 | Watanabe | 348/70 |
| 6,002,425 A | * | 12/1999 | Yamanaka et al. | 348/68 |
| 6,059,722 A | * | 5/2000 | Matumoto et al. | 600/178 |
| 6,078,353 A | * | 6/2000 | Yamanaka et al. | 348/65 |
| 6,120,435 A | * | 9/2000 | Eino | 600/118 |
| 6,219,091 B1 | * | 4/2001 | Yamanaka et al. | 348/65 |
| 6,533,722 B2 | * | 3/2003 | Nakashima | 600/179 |
| 6,629,925 B2 | * | 10/2003 | Kurosawa et al. | 600/180 |
| 2005/0220447 A1 | * | 10/2005 | Ito | 396/17 |
| 2006/0198620 A1 | * | 9/2006 | Watanabe | 396/17 |

FOREIGN PATENT DOCUMENTS

| | | |
|---|---|---|
| JP | 63-228118 | 9/1988 |
| JP | 9-90240 | 4/1997 |
| JP | 11-281902 | 10/1999 |
| JP | 3370871 | 11/2002 |
| JP | 3398550 | 2/2003 |

OTHER PUBLICATIONS

English Language abstract of 10-118019, pub. date: Dec. 5, 1998.
English Language abstract of 10-85175, pub. date: Jul. 4, 1998.

* cited by examiner

*Primary Examiner* — Chan S Park
*Assistant Examiner* — Jacky X Zheng
(74) *Attorney, Agent, or Firm* — Greenblum & Bernstein, P.L.C.

(57) ABSTRACT

An electronic endoscope has a video-scope with an image sensor, a light source, a signal reading processor, a shading member, a driver, and a driving controller. The signal reading processor alternately reads odd-line image-pixel signals and even-line image-pixel signals over one-frame reading interval, when forming a still image on the basis of one frame worth of image-pixel signals generated by a one-time exposure. The shading member blocks the illuminating light. The driver selectively arranges the shading member at a non-shading position that enable the illuminating light to pass and at a shading position that blocks the light. The driving controller controls the driver by a sequence of pulse signals so as to position the shading member at the shading position for a shading-interval in the one-frame reading interval, and so as to position the shading member at the non-shading position for a remaining reading-interval.

4 Claims, 4 Drawing Sheets

ELECTRONIC ENDOSCOPE HAVING AN APPARATUS FOR CONTROLLING A SHADING MEMBER

BACKGROUND OF THE INVENTION

1. Field of the Invention

The present invention relates to an electronic endoscope having a video-scope and a video-processor, especially, it relates to a shading or blinding member that is used when displaying or recording a still image.

2. Description of the Related Art

In an electronic endoscope, an interline-transfer CCD (IT CCD) is used to display a movie image on a monitor, wherein odd field image-pixel signals and even field image-pixel signals are alternately read from the CCD for one-field reading interval. When displaying or recording a still image generated by a one-time exposure, a shading or blind member is driven so as to shade the light that is directed to an object for one-field reading interval. Thus, odd-line image-pixel signals and even-line image-pixel signals are read from the CCD in order, for one-frame reading interval, so that a high-quality still image is obtained without a blur. The shading member is driven by an actuator, such as a DC motor.

SUMMARY OF THE INVENTION

An object of the present invention is to provide an electronic endoscope that is capable of effectively driving and controlling a shading member to obtain a still image.

An electronic endoscope according to the present invention has a video-scope with an image sensor, a light source, a signal reading processor, a shading member, a driver, and a driving controller. For example, the image sensor is an interline-transfer type CCD, wherein odd-field image-pixel signals and even-field image-pixel signals are alternately read from the CCD, when displaying a movie image. The light source radiates illuminating light. The signal reading processor alternately reads odd-line image-pixel signals and even-line image-pixel signals over one-frame reading interval, when forming a still image on the basis of one frame worth of image-pixel signals generated by a one-time exposure. As for the adjustment of an exposure-time, for example, a rotary shutter is provided. The rotary shutter has an aperture and a shading portion, which are formed so as to alternately pass and shade or block illuminating light, and the rotary shutter rotates at a constant speed.

The shading member blocks the illuminating light. For example, a plate-shaped shading member is provided between the light source and a light-guide, or fiber-optic bundle. The driver selectively arranges the shading member at a non-shading position that enables the illuminating light to pass and at a shading position that blocks the light. For example, the driver has a DC solenoid that moves the shading member between the non-shading position and the shading position. When using the rotary shutter, the driver arranges the shading member at the shading position so as to cover the aperture.

The driving controller controls the shading member so as to position the shading member at the shading position for a shading-interval in one-frame reading interval, and so as to position the shading member at the non-shading position for the remaining reading-interval. Then, the driving controller according to the present invention controls the driver by outputting a sequence of pulse signals to the driver. For example, the driving controller has a PWM controller, such as a push-pull type or full-bridge type PWM controller, which moves the driver forwards and backwards. As the sequence of pulse signals (not constant level signal) is output to the driver while positioning the shading member, consumption of electric power decreases and generation of heat is prevented. A control of a motion of the shading member and torque required for holding the shading member, is adjusted in accordance with a duty ratio of the sequence of pulse signals.

For example, the driving controller outputs a first sequence of pulse signals and a second sequence of pulse signals to the driver. The driver moves the shading member from the shading position to the non-shading position and holds the shading member at the shading position, based on the first sequence of pulse signals. On the other hand, the driver moves the shading member from the non-shading position to the shading position and holds the shading member at the non-shading position, based on the second sequence of pulse signals. To position the shading member rapidly and smoothly, the first and second sequence of pulse signals are respectively set to a sequence of pulse signals wherein a duty ratio of a head pulse signal is larger than that of the other pulse signals. The duty ratio is defined such that the shading member moves to the non-shading position or the shading position based on a constant level signal.

BRIEF DESCRIPTION OF THE DRAWINGS

The present invention will be better understood from the description of the preferred embodiment of the invention set fourth below together with the accompanying drawings, in which.

DESCRIPTION OF THE PREFERRED EMBODIMENTS

Hereinafter, the preferred embodiment of the present invention is described with reference to the attached drawings.

Figure 1:
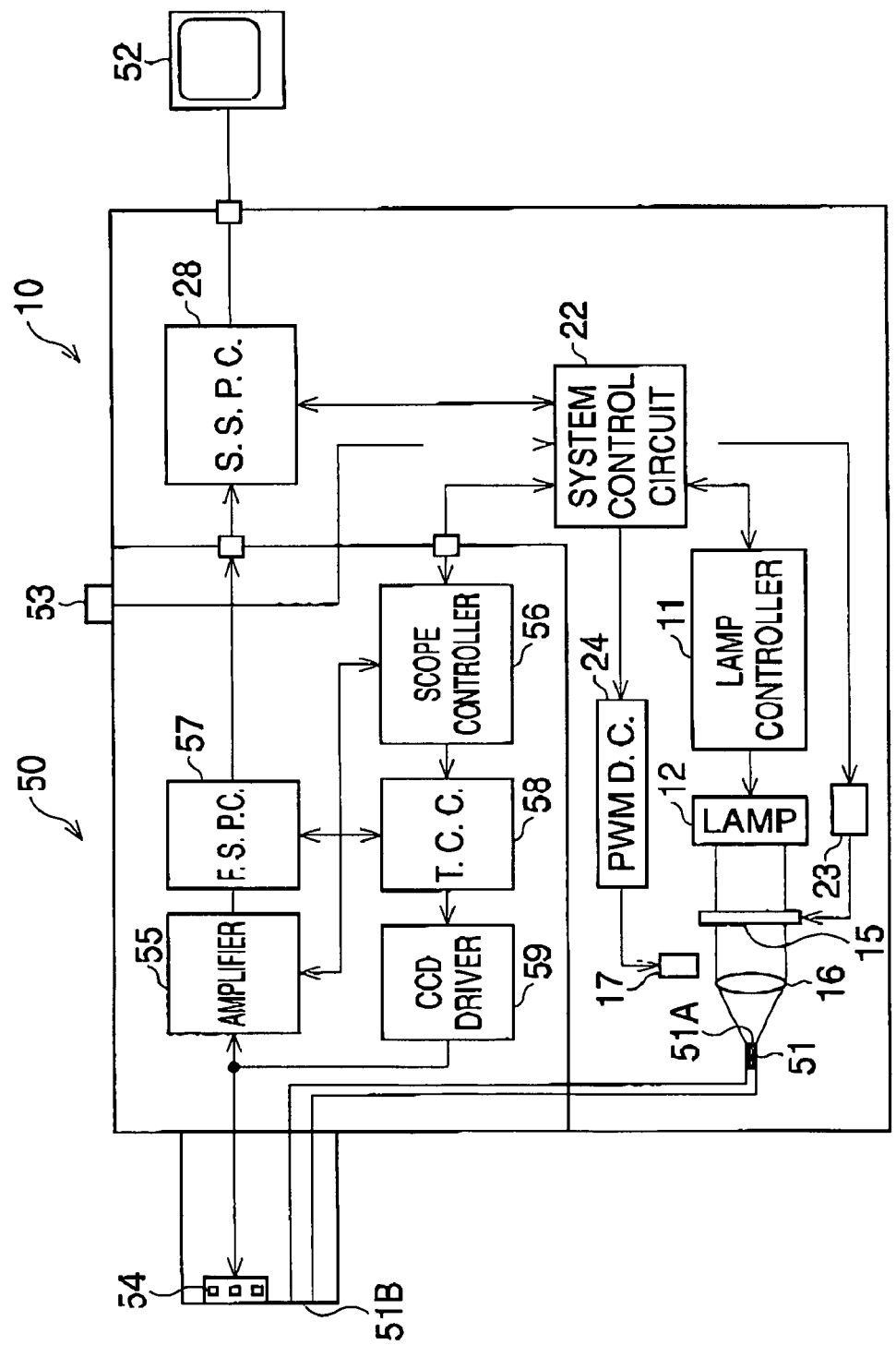
FIG. 1 is a block diagram of an electronic endoscope according to the present embodiment.

FIG. 1 is a block diagram of an electronic endoscope according to the present embodiment.

The electronic endoscope has a video-scope 50 with a CCD 54, and a video-processor 10, which has a lamp 12 and processes image-pixel signals read from the CCD 54. The video-scope 50 is detachably connected to the video-processor 10, and a monitor 52 is connected to the video-processor 10.

When a lamp switch button (not shown) is turned ON, a lamp controller supplies electric power to the lamp 12 so that the lamp 12 radiates illuminating light. Light emitted from the lamp 12 enters the incidence surface 51A of a light-guide 51 via a rotary shutter 15 and a collecting lens 16. The light-guide 51 is constructed of a fiber-optic bundle directing the light to a tip end of the video-scope 10. The light exits from the end portion 51B of the light-guide 51, and illuminates an observed object via a diffusion lens (not shown).

Light, reflected on the object, reaches the CCD 54 via an object lens (not shown), so that an object image is formed on the photo-sensitive area of the CCD 54. A color filter, checkered by four color elements of Yellow (Y), Magenta (M), Cyan (C), and Green (G), is arranged on the photo-sensitive area such that the four color elements are opposite to pixels arranged in the photo-sensitive area. Based on the light passing through each color element, analog image-pixel signals are generated by the photoelectric transformation effect. The generated image-pixel signals are read from the CCD 54 at regular time intervals in accordance with clock pulse signals output from a CCD driver 59. A timing control circuit 58 adjusts an output-timing of the clock pulse signals.

The CCD 54 is an interline-transfer CCD, and as for the color imaging method using an on-chip color filter, a so called "color difference lines sequential system" is applied. Therefore, while displaying a movie image, photo-generated charges in pixels neighboring each other are mixed, and odd-field image-pixel signals and even-field image-pixel signals are alternately read from the CCD 54 for one-field reading interval. The NTSC standard is herein applied as the TV standard, accordingly, the odd or even field image-pixel signals are read from the CCD 54 at a 1/60 second time interval, and are then fed to an amplifier 55. Note that, a PAL method may be applied instead of the NTSC method. In this case, the odd or even field image-pixel signals are read from the CCD 54 at a 1/50 second time interval.

The image-pixel signals are amplified in the amplifier 55 and are subjected to various processes, such as an amplifying process, a white balance process, and so on, in a first signal processing circuit 57 so that digital image signals are generated and are fed to a second signal processing circuit 28. In the second signal processing circuit 268, video signals are generated and output to the monitor 52 so that the observed image is displayed on the monitor 52.

On the other hand, when displaying or recording a still image on the monitor 52 by depressing a freeze button 53 on the video-scope 50, one-frame reading process, wherein one frame worth of image-pixel signals generated by a one-time exposure, is performed. Namely, when electric charges are accumulated by a one time exposure, image-pixel signals corresponding to an odd-line in the pixel-array are read from the CCD 54 over one-field reading interval, next, image-pixel signals corresponding to an even-line in the pixel-array are read from the CCD 54 over one-field reading interval. One field worth of odd-line image-pixel signals and one field worth of even-line image-pixels signals are respectively fed to the amplifier 55, the first signal processing circuit 57, and the second signal processing circuit 28. Thus, the still image is displayed on the monitor 52.

A system control circuit 22 includes a CPU controls each circuit, and then outputs control signals to the lamp controller 11, the second signal processing circuit 28, and so on. A timing control circuit in the video-processor 10 (not shown) outputs clock pulse signals to each circuit in the video-processor 10, to adjust a process-timing.

A scope controller 56, provided in the video-scope 50, controls the first signal processing circuit 55 and the timing control circuit 58. The timing control circuit 58 outputs driving signals to the CCD driver 59 in accordance with the control signals, which are output from the scope controller 56.

The rotary shutter 15 is attached to a motor (not shown), and rotates at a constant speed on the basis of driving signals fed from a motor driver 23. A chopper 17, which shades or blocks the light to be directed to the end portion of the video-scope 50, is provided between the rotary shutter 15 and the collecting lens 16, and has a DC solenoid (herein, not shown). The chopper 17 motions in accordance with a series of pulse signals fed from a PWM driving circuit 24.

Figure 2:
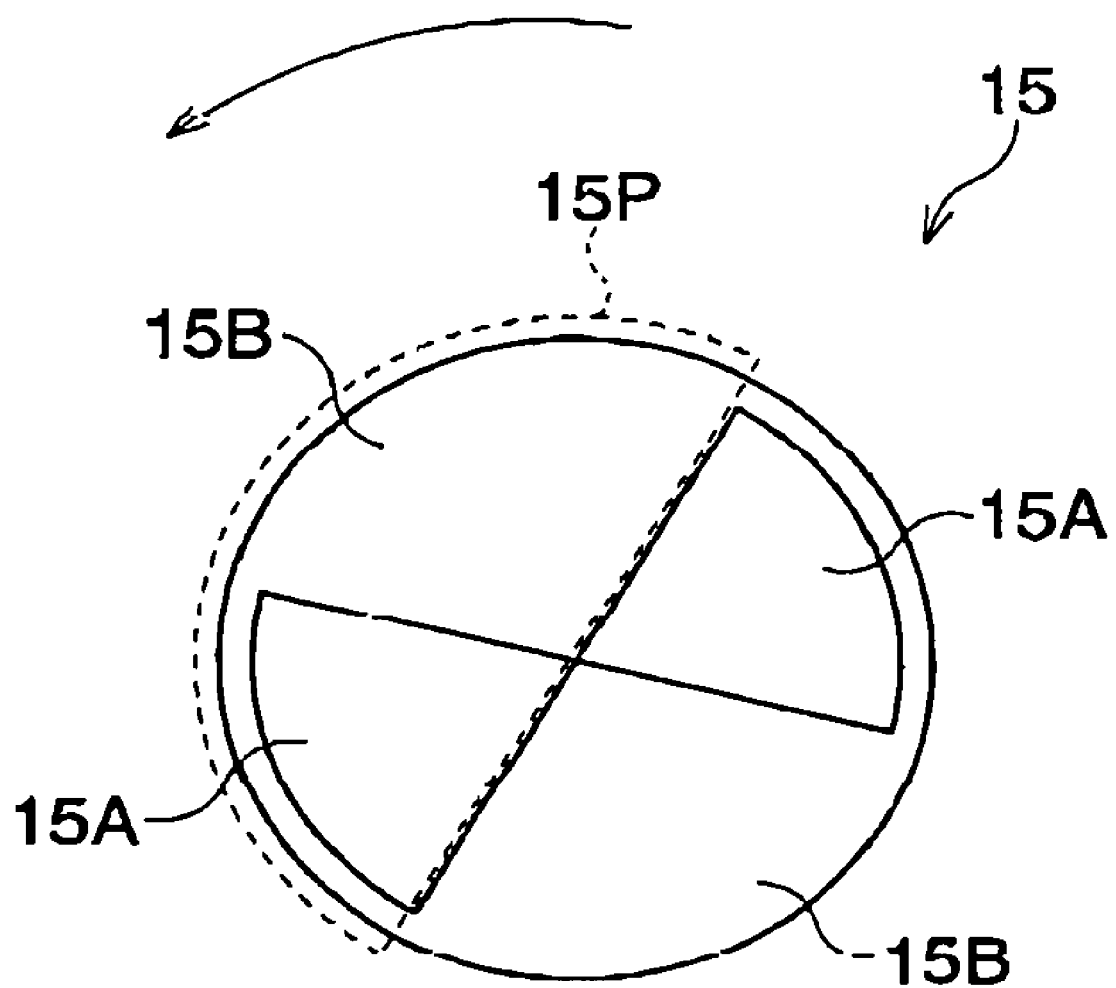
FIG. 2 is a plan view of the rotary shutter.
Figure 3:
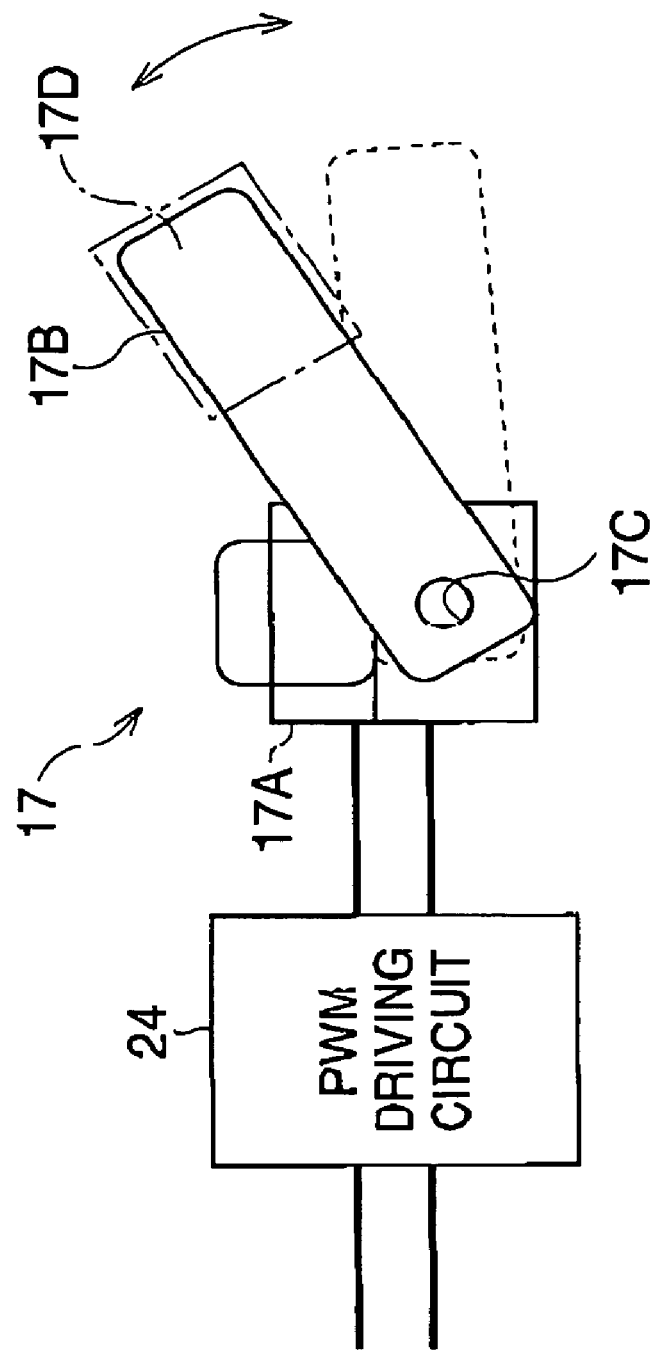
FIG. 3 is a plan view of the chopper.

FIG. 2 is a plan view of the rotary shutter 15. FIG. 3 is a plan view of the chopper 17.

The rotary shutter 15 is constructed of an aperture 15A that passes the light from the lamp 12 and a shading portion 15B that shades or shields the light. The aperture 15A is formed such that a pair of arc-shaped holes is opposite to each other. The rotary shutter 15 rotates by one-rotation in one-frame reading interval (herein, 1/30 second). Therefore, the half-circle 15P of the rotary shutter 15 corresponds to one-field reading interval (herein, 1/60 second). While the rotary shutter 15 rotates by a half-rotation, the aperture 15A and shading portion 15B passes the light-pass of the light emitted from the lamp 12, in turn. Thus, an exposure interval and a shading interval are alternately occurs in one-field reading interval, and this functions like an electronic shutter.

When displaying and recording the still image, one frame worth of image-pixel signals is obtained by light passing through one aperture 15A, namely, by rotating the rotary shutter 15 by a half-rotation. Then, the obtained one frame worth of image-pixel signals is read from the CCD 54 over the one-frame reading interval (=1/30 second). Since the other aperture 15A passes the light-path for the remaining interval, namely, 1/60 second, the chopper motions so as to blocks the illuminating light when the other aperture 15A passes the light-path.

In FIG. 3, the non-shading position of the chopper 17, which enables the light to pass trough one arc-shaped hole of the aperture 15A, is shown by a solid line, whereas the shading position of the chopper 17, which blocks the light when the other arc-shaped hole of aperture 15A passes the light-path, is shown by a broken line. The chopper 17 is a pivot-type solenoid and has a DC solenoid 17A and a plate member 17B that pivots around a center axis 17C. When the chopper 17 motions so as to shade the illuminating light, an end portion 17D of the plate member 17B covers the light-path or the aperture 15A of the rotary shutter 15. The PWM driving circuit 24 is a PWM controller, which outputs a sequence of pulse signals to the solenoid 17A. The PWM driving circuit 24 is a full-bridge PWM driver, which allows the plate member 17S to intermittently move or reciprocate between the non-shading position and the shading position, in accordance with two sequences of pulse signals as described later. Hereinafter, two pulse signals are respectively designated as "A" signals and "B" signals.

Figure 4:
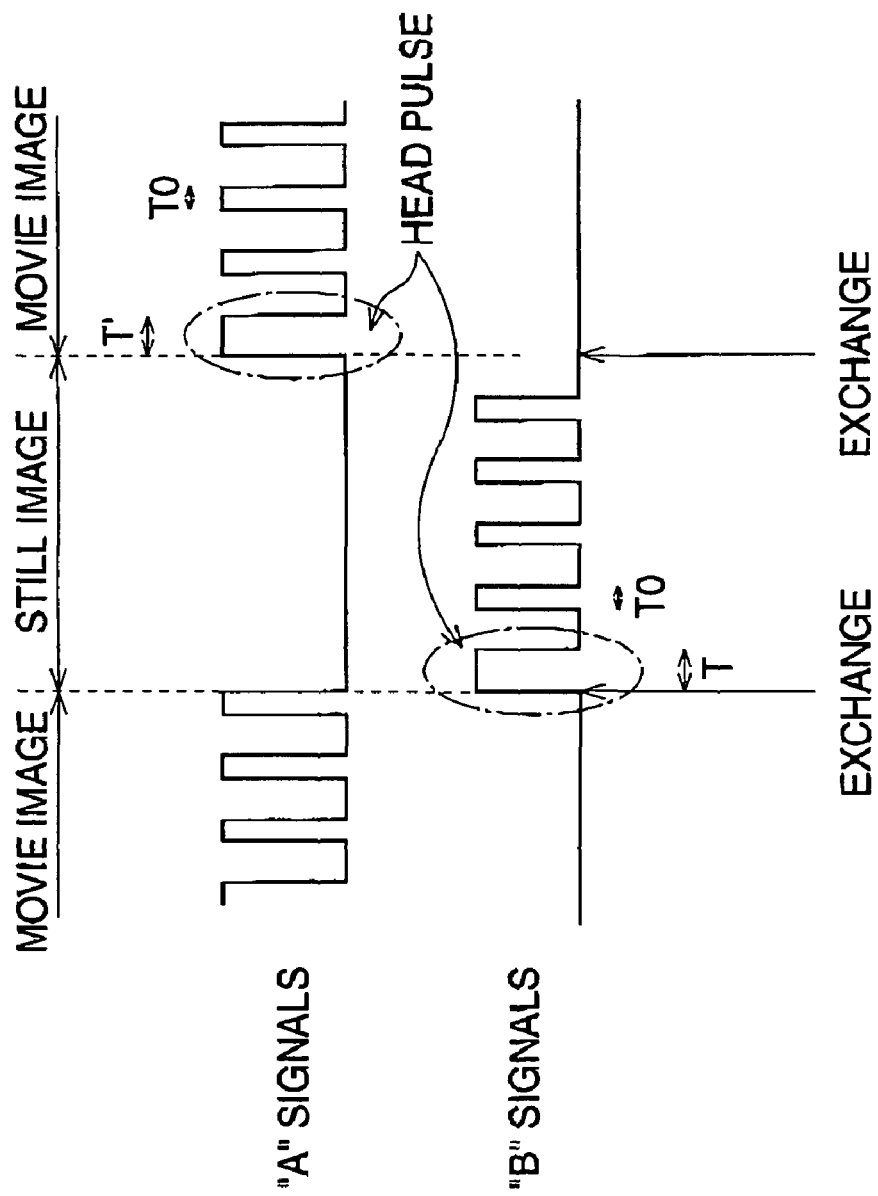
FIG. 4 is a timing chart of a sequence of pulse signals fed to the chopper.

FIG. 4 is a timing chart of a sequence of pulse signals fed to the chopper 17.

The plate member 17B is not supported, argued, or biased by any member, such as a elastic member, therefore, if the plate member 17B is not driven by the solenoid 17A, the plate member 17B is unstable and cannot be positioned at a given position. As shown in FIG. 4, while displaying the movie image, a sequence of pulse signals, which has a given duty ratio, is output from the PWM driving circuit 24 to the solenoid 17A as "A" signals. The "A" signals of the sequence of pulse signals pivot the plate member 17B from the shading position to the non-shading position, and the plate member 17B is securely held or positioned at the non-shading position. On the other hand, low-level signals are output from the PWM driving circuit 24 to the solenoid 17A as "B" signals.

When displaying and recording the still image by the freeze operation, a sequence of pulse signals are output to the solenoid as the "B" signals, whereas low-level signals are output to the solenoid as the "A" signals. The "B" signals (sequence of pulse signals) pivot the plate member 17B from the non-shading position to the shading position, and hold or position the plate member 17B at the shading position. As shown in FIG. 4, a pulse width "T" of a head pulse in the sequence of pulse signals is larger than the pulse width "T0" of the other pulse, namely, a duty ratio of the head pulse is larger than that of the other pulse. The pulse width "T" is defined in accordance with a time that the plate member 17B moves from the non-shading position to the shading position.

After the plate member 17B arrives at the shading position, a sequence of pulse signals having the same pulse width "T0" is input to the solenoid 17A.

When displaying the movie image again, the "A" signals of the sequence of pulse signals are output to the solenoid 17A to shift the plate member 17B from the shading position to the non-shading position, and the low-level "B" signals are output to the solenoid 17A. At this time, the pulse width "T'" of the head pulse for the "A" signals is larger than the other pulse width "T0". Namely, the duty ratio of the head pulse is larger than that of the other pulses. The pulse width "T'" is herein equal to the pulse width "T" (shown by the above explanation) and is defined in accordance with a time that the plate member 17B moves from the shading position to the non-shading position.

In this way, in the present embodiment, the chopper 17 including the solenoid 17A and the plate member 17B is controlled by the PWM driving circuit 24, which controls the chopper 17 by outputting the two sequences of pulse signals, "A" and "B" signals. When displaying the movie image, to hold the plate member at the non-shading position, the "A" signals are output to the solenoid 17A as a sequence of pulse signals, and the "B" signals, being low-level signals, are also output to the solenoid 17A. When displaying or recording the still image, the "B" signals are output to the solenoid 17A as a sequence of pulse signals, and the "A" signals being low-level signals are also output to the solenoid 17A.

Since the plate member 17A is held in a position by the sequence of pulse signals, namely, a constant level voltage is not applied to the solenoid 17A at all times, the consumption of electric power is lowered compared with a constant level signal, and generation of heat in the solenoid 17A is prevented. Also, the torque required for holding the plate member 17B and controlling a motion-speed of the plate member 17B can be adjusted by changing a duty ratio of the sequence of pulse signals. Since a constant level voltage is maintained while the plate member 17B moves from the non-shading position (shading position) to the shading position (non-shading position) by enlarging the duty ratio of the head pulse signal, the plate member 17B can be moved smoothly and rapidly while the plate member 17B moves.

Another solenoid may be applied instead of the DC solenoid, and another PWM controller may be applied instead of the full-bridge PWM controller.

Finally, it will be understood by those skilled in the art that the foregoing description is of preferred embodiments of the device, and that various changes and modifications may be made to the present invention without departing from the spirit and scope thereof.

The present disclosure relates to subject matters contained in Japanese Patent Applications No. 2004-301443 (filed on Oct. 15, 2004), which is expressly incorporated herein, by reference, in its entirety.

The invention claimed is:

1. An electronic endoscope including a video-scope with an image sensor, comprising:
a light source that radiates illuminating light;
a signal reading processor that alternately reads odd-line image-pixel signals and even-line image-pixel signals over a one-frame reading interval, when forming a still image based on one frame worth of image-pixel signals generated by a one-time exposure;
a shading member that blocks the illuminating light;
a driver comprising a solenoid that selectively arranges said shading member at a non-shading position that enables the illuminating light to pass and at a shading position that blocks the light;
a rotary shutter having an aperture and a shading portion which alternately pass and block the illuminating light, the rotary shutter rotating in accordance with the one-frame reading interval; and
a driving controller that controls said driver by outputting a sequence of pulse signals to the solenoid when forming a still image so as to position said shading member at the shading position for a shading-interval in the one-frame reading interval so as to cover the aperture, and position said shading member at the non-shading position for a remaining reading-interval.

2. The electronic endoscope of claim 1, wherein said driving controller outputs a first sequence of pulse signals and a second sequence of pulse signals to said driver, said driver moves said shading member from the shading position to the non-shading position and holds said shading member at the shading position by using the first sequence of pulse signals, and said driver moves said shading member from the non-shading position to the shading position and holds said shading member at the non-shading position by using the second sequence of pulse signals.

3. The electronic endoscope of claim 2, wherein the first and second sequences of pulse signals are sequences of pulse signals, each of the first and second sequences of pulses signals comprising a head pulse signal and other pulse signals, wherein a duty ratio of the head pulse signal is larger than a duty ratio of the other pulse signals.

4. An apparatus for adjusting an exposure of an electronic endoscope, comprising:
a shading member that blocks illuminating light emitted from a light source;
a driver comprising a solenoid that selectively arranges said shading member at a non-shading position that enables the illuminating light to pass and at a shading position that blocks the light;
a rotary shutter having an aperture and a shading portion which alternately pass and block the illuminating light, the rotary shutter rotating in accordance with a one-frame reading interval; and
a driving controller that controls said driver by outputting a sequence of pulse signals to the solenoid when forming a still image so as to position said shading member at the shading position for a shading-interval in the one-frame reading interval so as to cover the aperture, and to position said shading member at the non-shading position for a remaining reading-interval, when forming a still image based on one frame worth of image-pixel signals generated by a one-time exposure.

* * * * *